United States Patent [19]

Huck

[11] Patent Number: 4,548,087
[45] Date of Patent: Oct. 22, 1985

[54] COAL SAMPLING DEVICE

[75] Inventor: William R. Huck, Tuscaloosa, Ala.

[73] Assignee: Jim Walter Resources, Inc., Birmingham, Ala.

[21] Appl. No.: 627,946

[22] Filed: Jul. 5, 1984

[51] Int. Cl.⁴ .............................................. G01N 1/20
[52] U.S. Cl. ............................ 73/863.57; 73/863.52; 73/863.56; 141/114
[58] Field of Search ........... 73/863.52, 863.54, 863.56, 73/863.91, 863.92, 864.51, 863.43, 863.57; 141/114, 317, 10, 86

[56] References Cited

U.S. PATENT DOCUMENTS

| 632,713 | 9/1899 | Geissler . | |
|---|---|---|---|
| 1,063,725 | 6/1913 | Petersen | 73/863.57 |
| 1,646,032 | 10/1927 | Mason . | |
| 2,127,402 | 8/1938 | Gillican | 141/114 X |
| 2,525,113 | 10/1950 | Berg | 141/317 |
| 3,433,078 | 3/1969 | Thompson . | |
| 3,595,088 | 7/1971 | Meunier . | |
| 3,939,714 | 2/1976 | Miller, Jr. . | |
| 4,215,579 | 8/1980 | Hines et al. . | |
| 4,240,474 | 12/1980 | Perkins | 141/317 X |

FOREIGN PATENT DOCUMENTS

| 827400 | 11/1969 | Canada | 73/863.56 |
|---|---|---|---|
| 2854890 | 6/1979 | Fed. Rep. of Germany | 73/863.43 |
| 985677 | 3/1965 | United Kingdom | 73/863.57 |
| 1389124 | 4/1975 | United Kingdom | 73/863.56 |
| 983492 | 12/1982 | U.S.S.R. | 73/863.54 |

Primary Examiner—Stewart J. Levy
Assistant Examiner—Tom Noland
Attorney, Agent, or Firm—James W. Grace; Charles W. Vanecek

[57] ABSTRACT

This invention pertains to a device for taking samples of finely crushed particulate matter, such as coal from a flowing feed stream on a preset selection schedule, using a rotating drum which has one slot in its periphery and a receptable moveable into and out of the center area of the drum in alignment with said slot.

6 Claims, 3 Drawing Figures

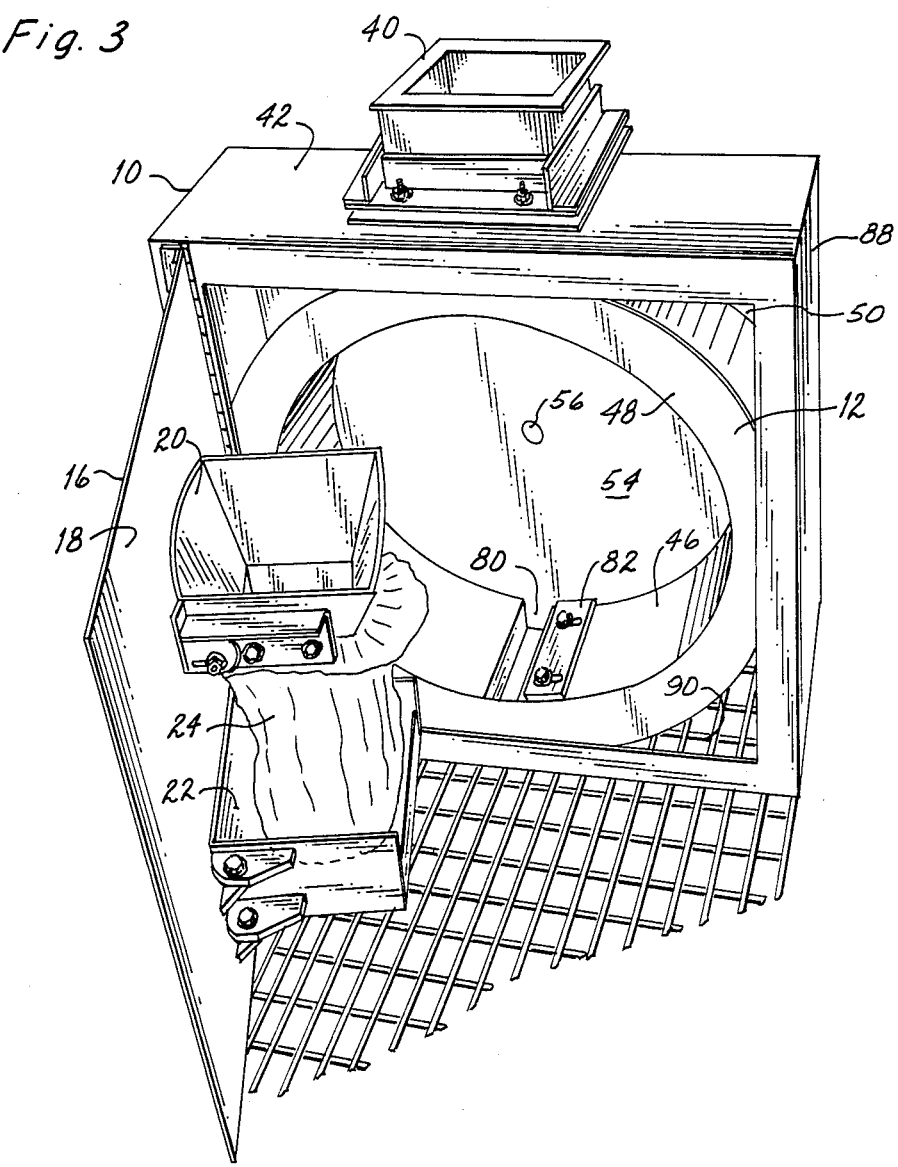

COAL SAMPLING DEVICE

This invention pertains to a device for taking samples of finely crushed particulate matter, such as coal from a flowing feed stream on a preset selection schedule, using a rotating drum which has one slot in its periphery and a receptable moveable into and out of the center area of the drum in alignment with said slot.

BACKGROUND OF THE INVENTION

1. Field of the Invention

This invention finds its greatest application in the field of finely crushed granular material and more particularly, the field of coal or ore mining.

2. Description of the Prior Art

The use of sampling devices for selectively taking samples of finely ground particulate material, such as coal or ore is well known. Certain types of these devices are shown in U.S. Pat. Nos. 632,713; 1,646,032; 3,433,078; 3,595,088; 3,939,714; and 4,215,579. Some of these devices are useful for grain products and some others are useful for fluid slurries. The latter are not necessarily useful with drier particulate matter. Each of these devices of the prior art has deficiencies which makes it less than optimal for the selection of samples of granular material.

In the practical application of the coal sampling device, it has been found that the feed stream from which the sample is taken consists of fine, moist granules which have a tendency to stick to surfaces on which they fall. Thus, the particular problem faced in the selection of coal samples is not usually found in the gathering of samples of dry grains, seeds or cereals or in the gathering of samples from liquid slurries.

One of the main drawbacks of the devices of the prior art teachings is the fact that the sample is not taken directly from the source which selects the sample but the sample is deposited on a chute or inclined trough to flow toward a receptacle. This deficiency is easily seen in those devices where the selected sample flows down a chute to discharge or where the sample can flow against the inside surface of the selection drum or wheel. In these cases, the samples taken may stick to the surface of the chute or the inside surface of the drum and require a cleaning operation for the chute or trough. In additon, the sample may build up even to the point of clogging up the chute.

The present invention avoids these problems by permitting the sample to flow directly into a bag or other receptacle without an intermediate chute or discharge surface to traverse. In addition, the apparatus of the present invention is fully enclosed so that the sample is collected without concern for air drafts which are present in well ventilated coal mines. The dust problem which is always present in a coal mine is diminished because the apparatus is enclosed.

The device can be easily adjusted to vary the size of the sample and the number of samples selected per unit of time.

The device of the invention is used in an environment in which the selection process takes place over an 8-hour period and takes samples from a primary stream of 400 tons per hour.

SUMMARY OF THE INVENTION

The invention comprises a device which has a rotating drum with an adjustable slot through its periphery. A bag or other receptacle is mounted inside the drum directly below the slot to receive the selected sample from a stream of particulate matter which is flowing toward and around the outer periphery of the drum from a conveyor. Means are provided to grant easy access to the receptacle for its removal and replacement by another receptacle.

OBJECTS OF THE INVENTION

It is an object of the present invention to provide a device which can select samples from a feed stream of particulate matter in a preselected cycle.

It is further object of the present invention to provide a device for selecting samples from a feed stream of particulate matter which can be easily adjusted to select different size samples.

It is another object of the present invention to provide a device for selecting samples from a feed stream of particulate matter in which the main stream flows over and around the periphery of a selection drum and unselected material joins the general flow of particulate material.

It is yet another object of the present invention to provide a device for selecting samples from a feed stream of particulate material in which the selected sample is discharged into a receptacle in an almost unobstructed stream.

These and other objects and advantages of the invention will become apparent to those skilled in the art from a consideration of the attached drawings in which like numerals indicate like elements and in which:

BRIEF DESCRIPTION OF THE DRAWING

FIG. 3 is a perspective view of an alternate mechanism to place a receptacle in the center of a rotating selection drum.

DESCRIPTION OF THE PREFERRED EMBODIMENT

Figure 1:
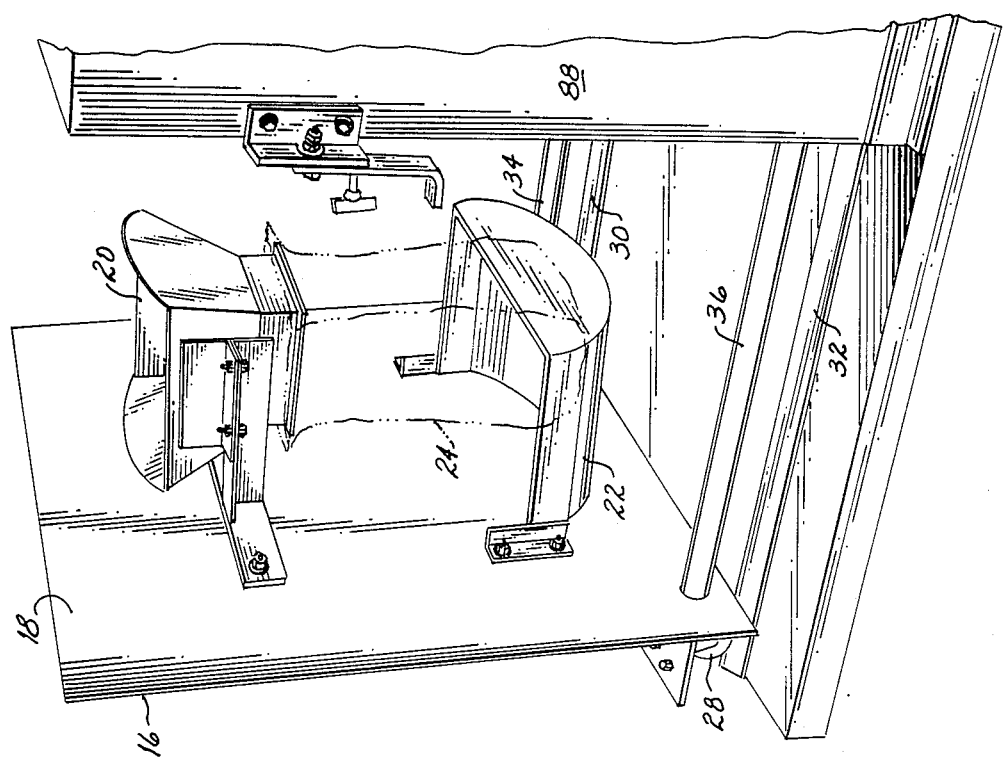
FIG. 1 is a perspective view of the device of the invention.
Figure 2:
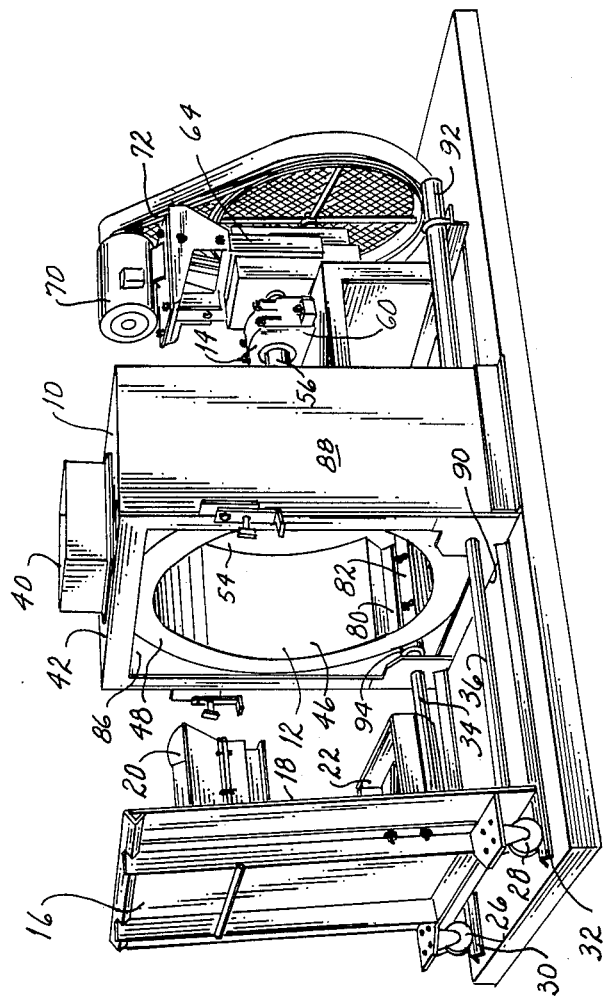
FIG. 2 is a perspective view of a detail of the invention showing a receptacle mounted on a reciprocating wall for catching selected material.

In the embodiment of FIG. 1, there is shown a housing 10 which encloses a rotating drum 12, drive means 14 connected to said drum 12 for supporting said drum inside said housing 14 and for rotating said drum at a preselected rotational velocity. A wall 16 is arranged to reciprocate on a track to expose the drum or close off the housing 10 depending upon the function of the wall desired at any given time. The side 18 of wall 16 (shown also in FIG. 2) which faces drum 12 supports a receptacle mounting device comprising an open chute 20 and a receptacle support trough 22.

A bag or other receptacle 24 is held in place below the open bottom of chute 20 and rests on trough 22 to receive the samples of granular material selectively collected by drum 12.

Wheels 26 and 28 support wall 16 to allow reciprocal movement along a track 30 and 32 using pipes 34 and 36 as guides for the reciprocal movement.

A trough or hopper 40 is mounted in the upper or top wall 42 of housing 10 to allow granular material to flow into housing 10 and on top of and around the outer periphery of drum 12.

In the preferred embodiment of the coal sampling device of the invention coal in generally lump form from a mining operation (not shown) is fed to a crusher (not shown). The crusher, which may be a conventional hammer mill or other crushing device; such as that described in U.S. Pat. No. 4,215,579, serves to crush coal to a smaller generally uniform, granular form suitable for sampling.

The coal in granular form is delivered to hopper 40 by a conveyor belt (not shown) and the feed stream of granular coal flows through hopper 40 to fall upon and around the outer periphery of drum 12.

Drum 12, which may be of any suitable metal, such as cast iron or sheet metal, has a circular peripheral section 46 which is slightly narrower than the width of top wall 42 of housing 10. A flange 48 is welded along the front edge of section 46 to prevent granular material from flowing off the front of drum 12. Flange 48 need only be a few inches high. At the rear of drum 12 is a second flange 50 similar to flange 48 to prevent the flow of granular material off the rear of drum 12. The rear portion of drum 12 is closed by a circular plate 54 which may be welded around its perimeter to the inside of drum 12 to close off the rear of the drum. The center of plate 54 has a shaft 56 welded to it so as to provide support and permit rotation of drum 12. Shaft 56 is held in place by a bearing structure 60 in which it can rotate. Rotational movement is provided to shaft 56 and thus to drum 12 by a suitable transmission gear box 64. A prime mover in the form of a motor 70 is connected to the transmission box by a belt and wheel arrangement 72. If desired, a spider (not shown) may be welded to drum 12 to provide support and rigidity.

Drum 12 has a slot 80 cut through its perimeter. Slot 80 is parallel to the axis of drum 12. Slot 80 may be of any suitable width such as three or four inches wide. To one side of slot 80, a plate 82 is adjustably bolted to the inner surface of drum 12. By a conventional slot and bolt arrangement, plate 82, which conforms to the inner surface of drum 12, is made adjustable so that the width of slot 80 can be adjusted from full open to closed. This range of sizes permits a selection of the quantity of granular material allowed to fall through slot 80 for each revolution of drum 12.

Housing 10 forms a rectangular box-like structure with top wall 42, sidewalls 86 and 88 and a bottom wall 90. Bottom wall 90 may be in the form of a grille or mesh through which the granular material not selected for sampling will flow after falling off the outer periphery of drum 12.

To provide for the reciprocal movement of wall 16, two pipes 92 and 94 form receptacles into which pipes 34 and 36 move telescopically.

A conveyor (now shown) runs below bottom wall 90 to carry off the surplus granular material and, in general, discharge along with the uncrushed coal to a storage area (not shown).

OPERATION OF THE SAMPLING DEVICE

After the coal has been mined by conventional means, it is usually in an ungraded form having lumps of various sizes and some smaller granular material, even as fine as coarse grains. The coal is carried by conveyor belts to a storage area but a smaller portion of the first coal stream is directed to a crusher which reduces the coal to a generally uniform smaller grain size. The coal in granular form from the crusher is carried by conveyor belts to the hopper 40 at the top of housing 10.

In order to select samples from the granular material, the width of slot 80 in drum 12 has been previously set by adjustably fixing plate 82 in a preset position.

A bag or other suitable container 24 has been attached with its open mouth below chute 20. The bottom of the bag or container 24 rests on trough 22.

Wall 16 is moved to the right (FIG. 1) along tracks 34 and 36 to close housing 10. A suitable closing mechanism (not shown) may be used to lock wall 16 in place. The open mouth of chute 20 with the bag attached now lies inwardly below the upper portion of drum 12. The open mouth of chute 20 is such that it is slightly greater than the length of slot 80 so that when slot 80 is rotated to appear above chute 20, slot 80 overlies the open mouth of chute 20 and all of the granular material which falls through slot 80 falls through chute 20 into bag 24.

The prime mover is energized and through the drive mechanism rotates drum 12 to bring slot 80 to various positions within housing 10. When slot 80 is at its uppermost position, it lies directly below hopper 40 and allows granular material to flow from hopper 40 through chute 20 into bag 24. When slot 80 is out of alignment with hopper 40, none of the granular material falls into bag 24. Thus, it is seen that only a selected quantity of the feed stream through hopper 40 will fall into bag 24. The remainder of the granular material falling through hopper 40 will fall onto and around the periphery of drum 12 and fall through the bottom wall 90 which is a mesh or grille. This material falls onto a conveyor to be sent to storage with the rest of the mined coal.

As an alternative, wall 16 may be mounted in the fashion of a door rather than a reciprocating member. As shown in FIG. 3, wall 16 is mounted on hinges 102 for movement toward and away from the open end of housing 10 and a bag 24 is mounted in the manner previously discussed to receive the selected granular material falling through slot 80.

After bag 24 becomes full of granular material, it can be removed and replaced by merely moving wall 16 to an open position and handling the exposed bag.

While there has been illustrated and described a preferred and alternative embodiment of the invention, these are set forth in illustration of the invention and not as limitations of the invention. It will be apparent to those skilled in the art that changes may be made in the described embodiments without departing from the scope of the invention as set forth in the appended claims.

I claim:

1. A coal sampling device comprising means to create a feed stream a granular material, a housing having a top wall, an open mesh bottom wall, a rear wall, and two side walls and further having a front opening, said top wall having an opening adapted to receive said feed stream of granular material, said rear wall having a circular opening therein, a rotatable drum mounted for axial rotation within said housing, said drum having an open end and a closed end, said closed end being adapted to mate with said rear wall opening to form a partial closure for said rear wall, said drum further having a peripheral upstanding flange along its open end, said drum further having a slot in its periphery across the axial width of the drum, means for inserting and removing a receptacle from said open end of said drum and in registration with said slot when said slot is rotated to the highest position occupied by the rotating drum, said means for inserting and removing a receptacle from said open drum end further comprising a closure for the said open end of said housing, means connected to said drum for rotation thereof, whereby said feed stream flows over and around the outer peripheral surface of said drum located between the rear wall of the housing and said peripheral upstanding flange and when said slot is in alignment with said hopper a selected portion of said feed stream falls into said receptacle in a cyclical manner as the drum rotates.

2. The coal sampling device of claim 1 in which said means for inserting and removing said receptacle has a receptacle holding attached to the surface thereof facing said housing.

3. The coal sampling device of claim 2 in which said receptacle holding means comprises a chute having an open bottom and a receptacle supporting trough lying below said chute.

4. Ths coal sampling device of claim 1 in which means for inserting and removing siad receptacle is mounted for reciprocal movement toward and away from said front opening in said housing.

5. The coal sampling device of claim 1 in which said means for inserting and removing said receptacle is mounted for hinged movement toward and away from said housing.

6. The coal sampling device of claim 1 in which said drum has an adjustable plate to enable selection of the size of the slot.

* * * * *